(12) United States Patent
Saur et al.

(10) Patent No.: US 12,144,570 B2
(45) Date of Patent: Nov. 19, 2024

(54) ROBOTIC SURGICAL SYSTEM AND METHOD FOR CONFIGURING A SURGICAL ROBOT

(71) Applicant: Carl Zeiss Meditec AG, Jena (DE)

(72) Inventors: Stefan Saur, Aalen (DE); Christoph Hauger, Aalen (DE)

(73) Assignee: Carl Zeiss Meditec AG, Jena (DE)

( * ) Notice: Subject to any disclaimer, the term of this patent is extended or adjusted under 35 U.S.C. 154(b) by 519 days.

(21) Appl. No.: 16/986,241

(22) Filed: Aug. 5, 2020

(65) Prior Publication Data

US 2022/0039883 A1 Feb. 10, 2022

(51) Int. Cl.
*A61B 34/30* (2016.01)
*B25J 9/16* (2006.01)
(Continued)

(52) U.S. Cl.
CPC .............. *A61B 34/30* (2016.02); *B25J 9/163* (2013.01); *B25J 9/1671* (2013.01); *B25J 13/08* (2013.01); *B25J 15/0019* (2013.01); *G05B 13/0265* (2013.01); *G05B 13/04* (2013.01); *G16H 10/60* (2018.01); *G16H 20/40* (2018.01); *G16H 40/63* (2018.01); *G16H 50/20* (2018.01); *G16H 50/50* (2018.01); *A61B 2034/102* (2016.02); *A61B 2034/105* (2016.02); *A61B 2034/301* (2016.02);
(Continued)

(58) Field of Classification Search
CPC .............. A61B 34/30; A61B 2034/102; A61B 2034/105; A61B 2034/301; G16H 20/40; G16H 50/50; G16H 50/20
See application file for complete search history.

(56) References Cited

U.S. PATENT DOCUMENTS 5,704,791 A 1/1998 Gillio
9,754,371 B2 9/2017 Kateb et al.
(Continued)

FOREIGN PATENT DOCUMENTS

WO 9630885 A1 10/1996
WO 2019046602 A1 3/2019

OTHER PUBLICATIONS

NVIDIA Issac Robot Simulator, part 12, GTC 2017, last accessed at https://www.youtube.com/watch?v=oa_wkSmWUw on Nov. 8, 2020.
(Continued)

*Primary Examiner* — John R Downey
(74) *Attorney, Agent, or Firm* — Ewers IP Law PLLC; Falk Ewers

(57) ABSTRACT

A robotic surgical system for treating a patient includes a surgical robot with a moveable robot member, an actuator for moving the robot member to 6D poses in a surgical field and for driving the robot member to act in the surgical field, a robot sensor for providing robot sensor data, and a control device for controlling the actuator according to a control program and under feedback of the robot sensor data, a processing unit configured to provide the control program to the control device, and to include and utilize a virtual anatomical model, a virtual surgical robot simulating movement and driving of the robot member, a surgical simulator, a sensor simulator, and a machine learning unit to create the control program, the machine learning unit reading the sensor simulator, the virtual surgical robot, and the virtual surgical field and feeding the virtual surgical robot.

14 Claims, 2 Drawing Sheets

(51) Int. Cl.
    *B25J 13/08*     (2006.01)
    *B25J 15/00*     (2006.01)
    *G05B 13/02*     (2006.01)
    *G05B 13/04*     (2006.01)
    *G16H 10/60*     (2018.01)
    *G16H 20/40*     (2018.01)
    *G16H 40/63*     (2018.01)
    *G16H 50/20*     (2018.01)
    *G16H 50/50*     (2018.01)
    *A61B 34/10*     (2016.01)
    *A61B 90/00*     (2016.01)

(52) U.S. Cl.
    CPC . *A61B 2090/3735* (2016.02); *A61B 2090/378* (2016.02)

(56) References Cited

U.S. PATENT DOCUMENTS

| | | | |
|---|---|---|---|
| 11,045,271 B1* | 6/2021 | Tran | G16H 20/40 |
| 11,389,248 B1* | 7/2022 | Roh | G05B 13/0265 |
| 11,464,589 B1* | 10/2022 | Roh | G16H 40/20 |
| 2013/0218340 A1* | 8/2013 | Hager | B25J 9/1671 |
| | | | 700/257 |
| 2019/0065970 A1* | 2/2019 | Bonutti | A61B 5/021 |
| 2020/0249654 A1* | 8/2020 | Edwards | G05B 19/414 |
| 2022/0354597 A1* | 11/2022 | Kaouk | A61B 34/20 |

OTHER PUBLICATIONS

Reinforcement learning—Wikipedia article, last accessed at https://en.wikipedia.org/wiki/Reinforcement_learning on Nov. 8, 2020.
Simulated Surgical Systems—Robotic Surgery Simulator, last accessed at http://pxr.a8a.myftpupload.com/projects/ross/ on Nov. 8, 2020.
Da Vinci Education, last accessed at https://www.intuitive.com/en-us/products-and-services/da-vinci/education on Nov. 8, 2020.
Deep Reinforcement Learning in Pacman, last accessed at https://www.youtube.com/watch?v=QiIHGSYbjDQ on Nov. 8, 2020.
IMEC—Hyperspectral Imaging, last accessed at https://www.imec-int.com/en/hyperspectral-imaging on Nov. 8, 2020.

* cited by examiner

ROBOTIC SURGICAL SYSTEM AND METHOD FOR CONFIGURING A SURGICAL ROBOT

TECHNICAL FIELD

The present disclosure relates to a robotic surgical system for treating a patient. The robotic surgical system includes a surgical robot including a moveable robot member, at least one actuator for moving the robot member to 6D poses in a surgical field and for driving the robot member to act in the surgical field, at least one robot sensor for providing robot sensor data giving an actuator feedback signal and depending on conditions in the surgical field, and a control device for controlling the actuator according to a control program and under feedback of the robot sensor data. The robotic surgical system further includes a processing unit configured to provide the control program to the control device.

The present disclosure further relates to a method for configuring a surgical robot providing a surgical robot including a moveable robot member, at least one actuator for moving the robot member to 6D poses in a surgical field and for driving the robot member to act in the surgical field, at least one robot sensor for providing robot sensor data giving an actuator feedback signal and depending on conditions in the surgical field, and a control device for controlling the actuator according to a control program and under feedback of the robot sensor data.

BACKGROUND

Such robotic surgical system and a method are known from U.S. Pat. No. 9,754,371 B2 and from WO 2019/046602. WO 96/30885 describes a virtual surgery system, in which a surgical procedure is simulated using image data of a patient. Physical instruments a surgeon uses in performing an actual procedure are simulated.

SUMMARY

It is an object of the present disclosure to provide a robotic surgical system for treating a patient and a method for configuring the surgical robot.

The disclosure provides a robotic surgical system for treating a patient. The robotic surgical system includes a surgical robot and a processing unit.

The surgical robot moves in a surgical field to perform surgery on the patient. In exemplary embodiments, the surgery is a microsurgical intervention. The surgical field is a part of the patient which is treated by invasive surgery. In exemplary embodiments, the surgical field is a leg of the patient, an eye of the patient, a belly of the patient, a brain of the patient, a spine of the patient, etc. Surgical tools or other instruments like towels, clamps, tubes, etc., may be present in the surgical field. In exemplary embodiments, the surgical robot is configured to perform at least one of cataract surgery, retina surgery, neurosurgical surgery, ENT surgery, and reconstruction surgery. In exemplary embodiments, the surgical robot operates autonomously, which means that the surgical robot performs invasive surgical treatment on the patient without any external action. In other exemplary embodiments, the surgical robot operates non-autonomously, i.e., assists a surgeon.

The robotic surgical system has at least two operating modes: a learning mode and a practice mode. In the learning mode, the robotic surgical system learns a surgical process to be performed. This learning involves a virtual surgery. The virtual surgery simulates in a virtual 3D model the surgery to be performed later by the surgical robot on the patient. The processing unit simulates and optimizes the virtual surgery and sends a data file to a control processor of a control device including the surgical robot. The processing unit includes a simulating processor and is located in the surgical robot itself or, in exemplary embodiments, outside the surgical robot in a computer, in a network of computers or in a computing cloud. The simulating processor can be a GPU or a CPU. Because of the high requirements of the calculation, a GPU is preferred. In the learning mode, the surgical process to be performed may be specific which means that the surgery may be performed on exactly one individual patient. The surgical process to be performed may also be unspecific, which means that a learnt invasive surgery may be acted in the same way on different patients. For example, the surgical robot may perform a learnt cataract surgery on different eyes of individual patients. In this case a learning mode for each individual patient is not necessary. There is only one learning mode for several surgeries on individual patients in several practice modes. In the practice mode, the surgical robot performs the surgery on the patient in the surgical field driven according to the data file which is a control data file. Then the surgical robot uses data learnt in the learning mode.

The surgical robot includes the control processor and a moveable robot member which include in exemplary embodiments at least one of a robot arm, an endoscope, and a surgical tool, each driven by at least one actuator. The actuator may include an electrical motor or a coil which receives an electrical control signal from the control processor and moves the moveable robot member in the surgical field. The actuator moves the robot member to 6D poses, which means that there are up to three rotational and up to three translational dimensions. The term "6D pose" includes position and/or location of the robot member as well as orientation of the robot member in up to 6 dimensions (maximum 3 translation directions and rotation about 3 different axes).

To simulate the surgical robot in the learning mode the processing unit includes and utilizes a virtual surgical robot. The virtual surgical robot simulates movement and action of the (real) moveable robot member and the actuator with its kinematic and geometric characteristics by a virtual 3D model of the (real) robot. The simulated actuator moves the simulated robot member in 6D in the virtual surgical field by changing the robot member's position and/or orientation. In exemplary embodiments, the virtual surgical robot simulates the movement of the robot member and the actuator by using mathematic models.

The virtual surgical field simulates the (real) surgical field and includes a virtual anatomical model. The virtual anatomical model simulates the patient in form of a virtual 3D model. The virtual anatomical model provides the virtual surgical field as a part of the patient which is treated by the virtual surgery. In exemplary embodiments, the virtual surgical field simulates a leg of the patient, an eye of the patient, a belly of the patient, a brain of the patient, a spine of the patient, etc., by a virtual 3D model. Surgical tools or other instruments like towels, clamps, tubes, etc., may be simulated in the virtual surgical field as well. In exemplary embodiments, the virtual anatomical model further includes a 3D model of an environment, e.g., the operating room, ambient temperature, etc. In exemplary embodiments, the virtual anatomic model includes a 3D model of an individual surgeon or a surgical team. The virtual anatomical model may include a morphology of the patient as well as optic textures and haptic characteristics of the patient etc. Further, the virtual anatomical model may include a vascular system representing blood, vessels, liquids, etc. In exemplary embodiments, the virtual anatomical model additionally includes pre-surgical data of the patient. The pre-surgical data are collected before surgery and stored in a database. The pre-surgical data may be realized in form of additional information on the patient like OCT, CT, MR, US data, etc.

The processing unit additionally includes and utilizes a surgical simulator. The surgical simulator reads the virtual anatomical model and the virtual surgical robot regarding the simulated movement and driving of the robot member. Thus, the surgical simulator simulates the virtual interaction between the virtual surgical robot and the virtual anatomical model to perform a virtual invasive surgical treatment. For example, the virtual action of the virtual surgical robot causes a virtual reaction of the virtual anatomical model in the virtual 3D model. This virtual action and reaction in the surgical simulator corresponds to the action of the surgical robot and the reaction of the patient in the real life surgical field.

The surgical robot further includes at least one robot sensor. The robot sensor detects a state of the moveable robot member and of the actuator and creates sensor data giving an actuator feedback signal. The actuator feedback signal represents information about the actual state of the moveable robot member and the actuator, e.g., pose, temperature, etc. The actuator feedback signal depends on conditions of the surgical field, e.g., body temperature, cardiac status, pulse, blood pressure, type of tissue, stiffness of tissue, etc. The robot sensor may present the actuator feedback signal to a user for example on a monitor. In exemplary embodiments, the robot sensor includes at least one of a white light camera, an IR camera, an OCT sensor, an ultrasonic sensor, a fluorescence sensor, and a depth sensor. In exemplary embodiments, the robot sensor includes a camera including a magnifying optics.

In exemplary embodiments, the surgical robot additionally includes at least one patient sensor. The patient sensor detects a state of the patient caused by the action of the surgical robot and provides patient sensor data resulting in a patient feedback signal. The patient feedback signal represents conditions of the patient, e.g., body temperature, cardiac status, pulse, blood pressure, type of tissue, stiffness of tissue, etc. The patient sensor may visualize the patient feedback signal on the monitor. In exemplary embodiments, the robot sensor may detect a state of the patient and may provide the patient sensor data resulting in the patient feedback signal. For example, a camera representing the robot sensor provides pictures of the surgical robot (to create robot sensor data) and the patient to create patient sensor data resulting in the patient feedback signal. The pictures of the camera may be analyzed and changes in the pictures of the patient may be detected (i.e., there is a tumor or a hemorrhage in any picture, if there is a lens in the predetermined position within the eye, etc.). In exemplary embodiments, the patient feedback signal and the actuator feedback signal are presented to the user on the monitor. In exemplary embodiments, the robot and/or the patient sensor may be attached to or integrated into the surgical robot.

To measure the state of the virtual surgical robot and of the virtual anatomical model in the virtual surgery, the processing unit further includes and utilizes a sensor simulator. The sensor simulator creates simulated robot sensor data of the virtual surgical robot based on a virtual actuator feedback signal. In exemplary embodiments, simulated patient sensor data are based on a virtual patient feedback signal. Then, the sensor simulator creates virtual pictures of the virtual sensors which correspond to the real pictures of the real sensors visualized on the monitor.

The processing unit further includes and utilizes the machine learning unit including a machine learning module. The machine learning unit reads the sensor simulator, the virtual surgical robot, and the virtual anatomical model and feeds the virtual surgical robot to create the control program. Based on simulated data (created by the sensor simulator, the virtual surgical robot and the virtual anatomical model), the machine learning unit learns the virtual surgery in the machine learning process and improves the quality of the interaction between the virtual surgical robot and the virtual anatomical model. Typically, an aim of the surgical treatment is taken into account to determine quality of the virtual surgery. The aim of surgery can include, e.g., lens removal in cataract surgery, recovery of a broken leg, the recovery of an injured brain or spine, removal of a tumor, clipping of an aneurysm, etc.

Several approaches of machine learning processes in the machine learning unit are possible. The machine learning process will be described later in an example of a reinforcement learning process. Other machine learning processes, e.g., semi-supervised learning, active learning, etc. are possible as well.

Based on the simulated data the machine learning unit determines the influence of the virtual action of the virtual surgical robot on the virtual anatomical model in the virtual surgery and calculates a first reward. The first reward shows to which degree the aim of the surgery was reached. Based on the first reward the machine learning unit adapts the parameters of the virtual surgical robot, e.g., directions of translational and/or the rotational movement, pace of the movement, etc., and starts a next virtual surgery in the surgical simulator with adapted parameters. Thereafter, the virtual surgical robot is operated with the adapted parameters on the virtual anatomical model, the machine learning unit calculates a second reward which shows whether to which extend the aim of surgery was reached. Then the parameters of the virtual surgical robot are adapted by the machine learning unit, a next virtual surgery is performed, and a third reward is calculated and so on. In exemplary embodiments, the machine learning unit does not start the entire virtual surgery after adapting the parameters of the virtual surgical robot, but only a part of the virtual surgery. In other words, the parameter set of the virtual surgical robot may be changed just for a following step of the virtual surgery. As a result, iterative process several virtual surgeries with various parameters have been simulated and their rewards are calculated. The machine learning unit learns the virtual surgical process gaining the highest reward, and the processing unit transfers this virtual surgical process to the control processor of the control device. The machine learning unit may learn autonomously.

The machine learning unit may use a target cost function which gets minimized when the parameters of the virtual surgical robot are changed. An optimal set of parameters was obtained when the target cost function is on its minimum. To optimize a classification problem, e.g., the decision if there is a tumor or no tumor in the virtual anatomic model, wrong classifications get punished in the target cost function for example by quadratic costs. Other mathematic models like cross-entropy cost, exponential cost, Hellinger distance, Kullback-Leiber divergence, Itakura-Saito distance, etc., may be used to optimize the classification problem.

In exemplary embodiments, a best viewing mode is determined by the target cost function, for example, by minimizing reflexes in pictures created by the sensors, focusing on a center of a picture, maximizing a focus area in a center of a picture, maximizing an illumination, maximizing an image contrast, etc. In another exemplary embodiment, a best alignment mode is determined by the target cost function for example by maximizing a viewing field of the surgeon onto the surgical field by moving, i.e., a camera to generate pictures on an external monitor, maximizing a working space of the surgeon, prohibiting collisions by maximizing distances of the surgeon to other tools, maximizing ergonomics of the surgeon, prohibiting a maximum of zoom or focus in a microscope, etc.

By simulating various interventions and varying the parameters of at least one of the robot, the patient sensor, e.g., zoom and/or focus and/or light intensity and/or position etc., the machine learning unit learns the best parameter set for the virtual surgical robot performing the virtual surgery. The virtual surgical robot can for example learn to position itself to guarantee a surgeon in a virtual surgical procedure the best view on the virtual anatomical model.

In other exemplary embodiments, instruments or gestures are tracked by comparing the virtual action of the virtual surgical robot and the real action of the surgical robot based on the target cost function for example by maximizing an overlap between the real robot member and the virtual robot member, or by minimizing the distance between a distal end of the real robot member and the distal end of the virtual robot member. By simulating the interaction between the virtual surgical robot with its virtual robot member and the virtual anatomical model, the processing unit detects the tools of the virtual robot member and positions the virtual robot member based on the detected information. Not only tools of the virtual surgical robot may be recognized but also a position of fingers of the surgeon may be recognized to provide an integrated gesture recognition.

In exemplary embodiments, abnormalities may be recognized by the target cost function. The processing unit warns the surgeon when an abnormality is detected. In the surgical simulator various worst-case scenarios can be simulated and the machine learning unit trains an algorithm based on these worst-case scenarios to warn the user (i.e. the surgeon). Because of this virtual learning of worst-case scenarios and the transfer of the electrical control signal to the control processor, abnormalities occurring during the surgical treatment may be detected and the surgeon may be warned in time.

In another exemplary embodiment, different phases of the surgery can be detected by the target cost function in the machine learning unit by using the simulated sensor data. An algorithm for determining phases of the surgery is learned from virtual surgeries and transferred to the control device as the electrical control data file.

The control processor delivers the electrical control data file to the actuator according to a control program and under feedback of the actuator feedback signal and, in exemplary embodiments, under feedback of the patient feedback signal. The electrical control data file may be adapted in the control processor during the surgery based on this feedback.

The simulation can be expanded by adding a virtual 3D model of the operating room (where other devices, lamps, operating room staff, etc., are visualized) to avoid collisions of the moving virtual surgical robot and the environment. For this purpose, it is advantageous if the virtual anatomical model is additionally equipped with at least one sensor for detecting the surroundings (e.g., surrounding elements camera, depth sensor, etc.).

The method for configuring the surgical robot includes the step of providing the surgical robot including the moveable robot member, the at least one actuator for moving the robot member to 6D poses in the surgical field and for driving the robot member to act in the surgical field, the at least one robot sensor for providing robot sensor data giving an actuator feedback signal and depending on conditions in the surgical field, and the control device for controlling the actuator according to a control program and under feedback of the robot sensor data. The method for configuring the surgical robot further providing a virtual anatomic model including a virtual surgical field, and a virtual surgical robot by simulating movement and driving of the robot member. The method for configuring the surgical robot further includes the step of providing the surgical simulator reading the virtual anatomic model and the virtual surgical robot regarding the simulated movement and driving of the robot member, and the step of providing the sensor simulator creating simulated robot sensor data for the virtual surgical robot and the simulated patient sensor data based on an actual state of the virtual surgical robot and the virtual anatomic model fed by the surgical simulator. The method for configuring the surgical robot includes the step of reading signals from the sensor simulator, the virtual surgical robot and the virtual surgical field and includes the step of feeding the signals to the virtual surgical robot in a machine learning process. The method further finally includes the step of creating the control program by the machine learning process and supplying the control program to the surgical robot.

All units, models, virtual elements and virtual systems described herein, can be realized as software modules in a computer program which is executed on a computer including a processor and a RAM. Further, all electrical signals described herein may have the form of data files to be read by a processor of structural element to be controlled.

It goes without saying that the aforementioned features and those yet to be explained below can be used not only in the combinations specified but also in other combinations or on their own, without departing from the scope of the present disclosure.

BRIEF DESCRIPTION OF THE DRAWINGS

The disclosure will now be described with reference to the drawings wherein.

DESCRIPTION OF EXEMPLARY EMBODIMENTS

The disclosure will be explained in more detail below on the basis of exemplary embodiments, with reference being made to the attached drawings, which likewise disclose features essential to the disclosure. These embodiments serve merely as examples and should not be interpreted as restrictive. By way of example, a description of an exemplary embodiment with a plurality of elements or components should not be interpreted to the effect that all these elements or components are necessary for implementation. Rather, other exemplary embodiments also may contain alternative elements and components, fewer elements or components or additional elements or components. Elements or components of different exemplary embodiments can be combined with one another, unless indicated otherwise. Modifications and developments which are described for one of the exemplary embodiments may also be applicable to other exemplary embodiments. In order to avoid repetition, the same elements or corresponding elements in the various figures are denoted by the same reference signs and are not explained repeatedly.

Figure 1:
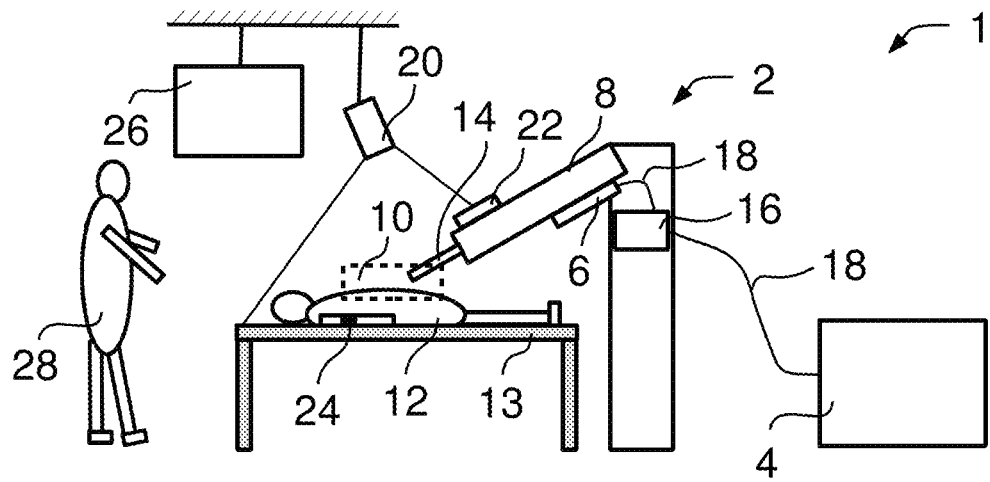
FIG. 1 shows surgical robotic system.

FIG. 1 shows a robotic surgical system 1 according to an exemplary embodiment of the disclosure. The robotic surgical system 1 includes a surgical robot 2 and a processing unit 4. The surgical robot 2 includes at least one actuator 6 which drives a moveable robot member 8 in a surgical field 10 which is located at a patient 12 lying on an operation table 13. The moveable robot member 8 is equipped with a surgical tool 14 and a control device 16 controlling the actuator 6 based on an electrical control data. The control device 16 is connected to the actuator 6, in case of FIG. 1 by electrical cables 18. The processing unit 4 is connected to the control device 16 by electrical cables 18 as well. Wireless connections are options. The surgical robot 2 additionally includes a camera 20 which may work as a robot sensor 22 and a robot sensor 22 which may be an OCT. The camera 20 may be attached to or integrated into the surgical robot 2. The camera 20 may be a surgical microscope. The surgical robot 2 additionally includes a patient sensor 24 attached to the patient 12. The camera 20 may work as patient sensor 24 as well. The robot sensor 22 and the patient sensor 24 are connected to a monitor 26 to show results of a measurement to a surgeon 28. The functioning of the robotic surgical system 1 shown in FIG. 1 will be explained step by step below. The camera 20 may include a magnification optics.

Figure 2:
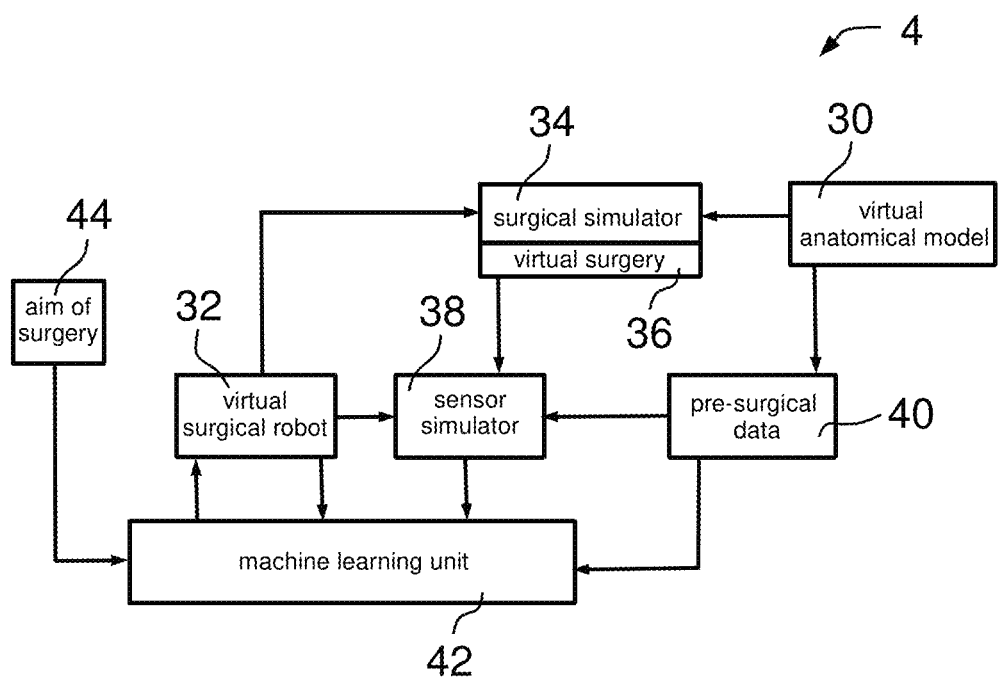
FIG. 2 shows learning mode of a robotic surgical system.

FIG. 2 shows the processing unit 4 as a part of the robotic surgical system 1. The processing unit 4 includes and utilizes a virtual anatomical model 30, a virtual surgical robot 32, a surgical simulator 34 creating a virtual surgery 36, a sensor simulator 38, simulated pre-op data 40, a machine learning unit 42, and information about an aim of surgery 44.

The robotic surgical system 1 can operate in a learning mode and in a practice mode. In the learning mode the robotic surgical system 1 learns an invasive surgical treatment to be performed by creating an electrical control data file in the virtual surgery 36. This electrical control data file is transferred to a control processor of the control device 16 by the processing unit 4. In the practice mode the surgical robot 2 performs surgery 46 in the surgical field 10 driven according to the data file which is a control data file. Then the surgical robot 2 uses data learnt in the learning mode. The data learnt in the learning mode may be used on a specific patient 12 or on more than one individual patient 12.

The surgical field 10 is a part of the patient which is treated by surgery 46. In exemplary embodiments, the surgery is a microsurgical intervention. In exemplary embodiments, the surgical field 10 are leg of the patient 12, eye of the patient 12, belly of the patient 12, a brain of the patient 12, a spine of the patient 12, etc. Surgical tools 14 or other instruments like towels, clamps, tubes, etc., may be present in the surgical field.

FIG. 2 shows the learning mode which is performed by the processing unit 4. The processing unit 4 includes a simulating processor and is located in the surgical robot 2 itself or, in exemplary embodiments, outside the surgical robot 2 in a computer, in a network of computers or in a computing cloud. The simulating processor may include a CPU or a GPU. Because of the high requirements of the calculation, a GPU is preferred.

The processing unit 4 includes and utilizes the virtual anatomical model 30 and the virtual surgical robot 32.

The virtual anatomical model 30 represents a patient 12 in form of a virtual 3D model. It provides a virtual surgical field representing the (real) surgical field 10 as part of the patient 12 which is treated by the virtual surgery 36. The virtual anatomical model 30 may include a morphology of the patient 12 as well as optic textures and haptic characteristics of the patient, etc., in form of the virtual 3D model. In exemplary embodiments, the virtual anatomical model 30 includes a virtual vascular system representing blood, vessels, liquids, etc. In exemplary embodiments, the virtual anatomical model 30 further includes the pre-surgical data 40 of the patient 12. The pre-surgical data are collected before surgery 46 and stored in a database. The pre-surgical data may be realized in form of additional information on the patient like OCT, CT, MR, US data, etc. In exemplary embodiments, the virtual surgical field further includes an environment of the virtual surgery 36 in form of a virtual 3D model. This environment includes, e.g., an operating room and/or the surgeon 28 and/or a surgical team.

The virtual surgical robot 32 simulates movement and action of the moveable robot member 8 and the actuator 6 to 6D poses with its kinematic and geometric characteristics by a virtual 3D model of the surgical robot 2. The virtual surgical robot 32 includes at least one of a robot arm, an endoscope, and a surgical tool 14. The virtual surgical robot 32 further includes at least one virtual actuator representing the actuator 6 for driving the moveable robot member 8 in form of the virtual 3D model. The actuator 6 may include an electric motor or a coil which receives an electrical control data file generated in the processing unit 4 and moves the moveable robot member 8 in the surgical field. The actuator 6 moves the moveable robot member 8 to 6D poses in the surgical field, which means that there are three directions of translational movement and three directions of rotational movement. The actuator 6 changes the position as well as the orientation of the robot member 8. The actuator 6 further drives the moveable robot member 8 to perform the surgery 46 autonomously or assist, i.e., the surgeon 28. This interaction of the moveable robot member 8 and the actuator 6 is simulated in the surgical simulator 34 in form of the virtual 3D model. The surgical simulator 34 further simulates an interaction between the surgical robot 2 and the patient 12. The processing unit 4 may simulate the movement of the robot member 8 and the actuator 6 by using mathematic models.

As shown in FIG. 2, the surgical simulator 34 reads the virtual anatomical model 30 and the virtual surgical robot 32 regarding the simulated movement and driving of the virtual robot member in the virtual surgical field. Based on this virtual input data the surgical simulator 4 performs the virtual surgery 36. In this virtual surgery 36 the virtual action of the virtual surgical robot 32 causes a virtual reaction of the virtual anatomical model 30 in form of a virtual 3D model. This virtual interaction corresponds to the action of the surgical robot 2 and the reaction of the patient 12 in the surgery 46. To measure the state of the virtual surgical robot 32 and the virtual anatomical model 30 in the virtual surgery 36, the processing unit 4 includes and utilizes the sensor simulator 38. The sensor simulator 38 simulates at least one robot sensor 22 of the surgical robot 2 and at least one patient sensor 24 of the patient 12 in form of a virtual 3D model.

The robot sensor 22 detects a state of the moveable robot member 8 and the actuator 6 and provides robot sensor data resulting in an actuator feedback signal which is presented to the surgeon 28 on the monitor 26. The actuator feedback signal represents information about the actual state of the moveable robot member 8 and the actuator 6, e.g., a pose, a temperature, etc., and depends on conditions of the surgical field 10, e.g., a cardiac status, a body temperature, a pulse, a blood pressure, a type of tissue, a stiffness of tissue, etc. In exemplary embodiments, the robot sensor 22 includes at least one of a white light camera, an IR camera, an OCT sensor, an ultrasonic sensor, a fluorescence sensor, and a depth sensor.

The patient sensor 24 provides patient sensor data which depends on conditions of the patient 12, e.g., a cardiac status, a body temperature, a pulse, a blood pressure, a type of tissue, a stiffness of tissue, etc. The action of the moveable robot member 8 causes a reaction of the patient 12 in the surgical field 10. This reaction is detected by the patient sensor 24. The patient sensor creates the patient sensor data resulting in a patient feedback signal. The patient feedback signal is presented to the surgeon 28 on the monitor 26. In exemplary embodiments, the patient feedback signal and the actuator feedback signal are both presented to the surgeon 28 on the monitor 26. In exemplary embodiments, the patient feedback signal may be created by the robot sensor 22.

As shown in FIG. 2, the information about the virtual surgery 36 in the surgical simulator 34 is delivered to the sensor simulator 38. The sensor simulator 38 additionally gets information directly from the virtual surgical robot 32 and the virtual anatomical model 30 added with the pre-surgical data 40. In the sensor simulator 38 the processing unit 4 creates simulated robot sensor data and simulated patient sensor data giving a simulated actuator feedback signal and a simulated patient feedback signal. The created simulated sensor data is transferred to the machine learning unit 42 as an electrical data file.

The machine learning unit 42 includes a machine learning module. The machine learning unit 42 reads the sensor simulator 38, the virtual surgical robot 32, the virtual anatomical model 30 added with pre-surgical data 40 and the aim of surgery 44 to create the control program and feeds the virtual surgical robot 32. By feeding the virtual surgical robot 32 the machine learning unit 42 enables another virtual surgery 46 to start in which parameters of the virtual surgical robot 32 are changed.

To detect parameters of the virtual surgical robot 32 to change for a virtual surgery 36 which achieves the aim of surgery 44 the most, the machine learning unit 42 learns based on the simulated sensor data in a machine learning process. Several approaches of machine learning processes may be used in the machine learning unit 42. In an exemplary embodiment, a reinforcement learning process is used in the machine learning unit 42, as described above.

In case of a reinforcement learning process, the machine learning unit 42 determines the influence of the virtual action of the virtual surgical robot 32 in the virtual surgery 36 and calculates a first reward which shows to which degree the aim of the surgery 44 was reached in the virtual surgery 36. Based on the first reward the machine learning unit 42 adapts the parameters of the virtual surgical robot 32, e.g., directions of translational and/or rotational movement, pace of movement, etc. and starts a second virtual surgery 36 in the surgical simulator 34 with adapted parameters. Based on the second virtual surgery 36 the machine learning unit 42 calculates a second reward which shows whether to which extend the aim of surgery 44 was reached. Then, the parameters of the virtual surgical robot 32 are adapted, a third virtual surgery 36 is done, and a third reward is calculated and so on. As a result, several virtual surgeries 36 with various parameters have been simulated and their rewards are calculated.

The machine learning unit 42 compares the rewards of the several virtual surgeries 36 and detects in which virtual surgery 36 the aim of surgery 44 is achieved the most. Based on the virtual surgery 36 which created the highest rewards the machine learning unit 42 creates the control program and transfers it to the control device 16 as the electrical control data file in which an optimal parameter setting for the surgical robot 2 is included. The machine learning unit 42 may learn autonomously. In exemplary embodiments, the machine learning unit 42 optimizes the parameters of the virtual surgical robot 36 by using a target cost function which gets minimized when the parameters are changed until an optimal set of parameters is reached, when the target cost function is on its minimum. Several approaches of the target cost function are possible, as described above.

Figure 3:
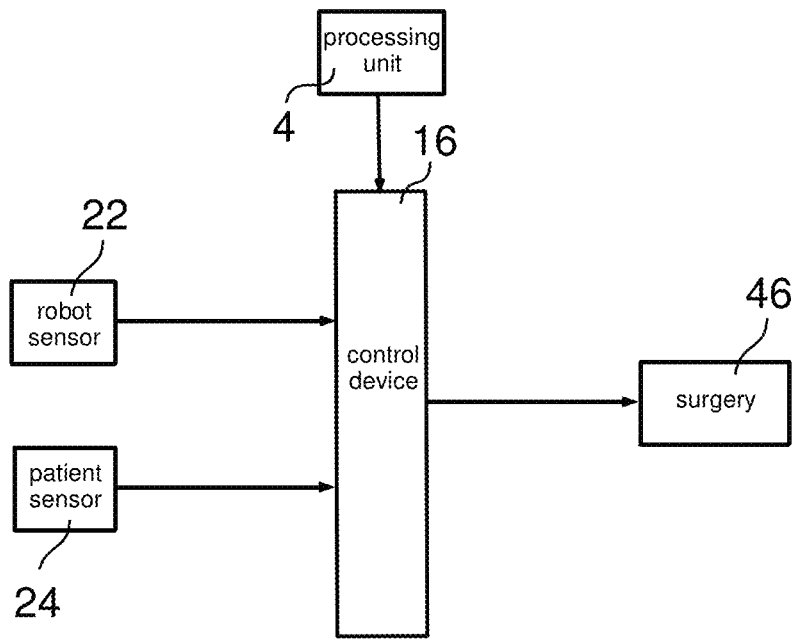
FIG. 3 shows practice mode of the robotic surgical system.

As shown in FIG. 3, the processing unit 1 provides the control program to the control device 16, which is a part of the surgical robot 2. In the practice mode the surgical robot 2 acts the surgery 46 as shown in FIG. 1. In the surgery 46 the surgical robot 2 includes the optimal parameter set virtually learned in the learning mode in the processing unit 4.

The surgical robot 2 includes the robot sensor 22 giving the actuator feedback signal and depending on the conditions in the surgical field 10 and the patient sensor 24 giving the patient feedback signal depending on the conditions of the patient 12. The control processor comprised by the control device 16 gets input from the patient sensor 24, the robot sensor 22 and the processing unit 4 (electrical control data file) resulting in an output of the surgery 46. The feedback signal (sent by the sensors 22, 24) is examined in the control device 16 in comparison with the control program. In exemplary embodiments, the surgery 46 may be optimized in the control device 16 based on the feedback signal delivered by the sensors 22, 24 during the surgery 46 on the patient 12.

The robotic surgical system 1 is used in at least one of cataract operation, retina operation, neurosurgical operation, ENT operation, and reconstruction operation.

Figure 4:
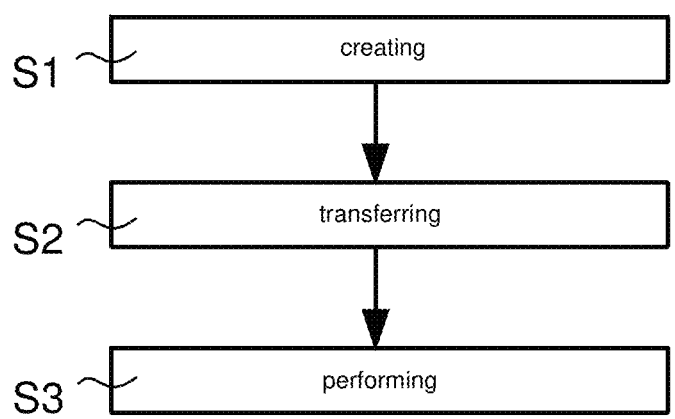
FIG. 4 shows a flow chart of a method for configuring a surgical robot.

Another aspect of the disclosure is to provide a method for configuring the surgical robot 2 as described above. A flow chart of the method for configuring the surgical robot 2 is shown in FIG. 4.

In a first step S1, the processing unit 4 creates the control program in the machine learning process. In step S1, the machine learning unit 42 determines the influence of the virtual action of the virtual surgical robot 32 in the surgical simulator 34 on the virtual anatomical model 30 and calculates the first reward which shows to which degree the aim of the surgery 44 is reached in the virtual surgery 36. Based on the first reward the machine learning unit 42 starts the second virtual surgery 36 in the surgical simulator 34. In this second virtual surgery 36 the parameters of the virtual surgical robot 32 are adapted by the machine learning unit 42. Based on this second virtual surgery 36 the second reward which shows whether to which extend the aim of surgery 44 is reached in the second virtual surgery 36 is calculated by the machine learning unit 42. Then, the parameters of the virtual surgical robot 32 are adapted and the third reward is calculated by the machine learning unit 42 and so on. As a result, several virtual surgeries 36 with various parameters of the virtual surgical robot 32 are simulated in the processing unit 4 and their rewards are calculated and compared. This machine learning process results in a control program including the parameters for the virtual surgical robot 32 which created the highest rewards.

In a step S2, the control program, created in the machine learning process in the processing unit 4, is transferred to the control device 16 as the electrical control data file.

In a step S3, the control processor of the control device 16 moves the actuator 6 to drive the surgical robot 2 in the robotic surgical system 1 to perform the surgery 46. In exemplary embodiments, the control program gets continuously optimized while performing the surgery 46 on the patient 12 under feedback of the robot sensor 22 and the patient sensor 24.

Various exemplary embodiments of systems, devices, and methods have been described herein. These exemplary embodiments are given only by way of example and are not intended to limit the scope of the claimed disclosures. It should be appreciated, moreover, that the various features of the exemplary embodiments that have been described may be combined in various ways to produce numerous additional embodiments. Moreover, while various materials, dimensions, shapes, configurations and locations, etc. have been described for use with disclosed exemplary embodiments, others besides those disclosed may be utilized without exceeding the scope of the claimed disclosures.

Persons of ordinary skill in the relevant arts will recognize that the subject matter hereof may include fewer features than illustrated in any individual exemplary embodiment described above. The exemplary embodiments described herein are not meant to be an exhaustive presentation of the ways in which the various features of the subject matter hereof may be combined. Accordingly, the exemplary embodiments are not mutually exclusive combinations of features; rather, the various exemplary embodiments can include a combination of different individual features selected from different individual exemplary embodiments, as understood by persons of ordinary skill in the art. Moreover, elements described with respect to one exemplary embodiment can be implemented in other exemplary embodiments even when not described in such exemplary embodiments unless otherwise noted.

Although a dependent claim may refer in the claims to a specific combination with one or more other claims, other exemplary embodiments can also include a combination of the dependent claim with the subject matter of each other dependent claim or a combination of one or more features with other dependent or independent claims. Such combinations are proposed herein unless it is stated that a specific combination is not intended.

What is claimed is:

1. A robotic surgical system for treating a patient, the robotic surgical system being autonomously controlled in a practice mode, the robotic surgical system comprising:
   a surgical robot comprising a moveable robot member and configured to perform a real surgical treatment on a patient in the practice mode;
   at least one actuator configured to move the moveable robot member to 6D poses in a surgical field and to drive the moveable robot member to act in the surgical field;
   at least one robot sensor configured to provide robot sensor data giving the at least one actuator a feedback signal and depending on conditions in the surgical field;
   a control device configured to control the at least one actuator according to control data and under feedback of the robot sensor data; and
   a processing unit comprising:
   a patient specific virtual anatomical model including a virtual surgical field;
   a virtual surgical robot simulating a movement and driving of the moveable robot member;
   a surgical simulator reading the patient specific virtual anatomical model and reading the virtual surgical robot regarding the movement and the driving of the moveable robot member;
   a sensor simulator creating simulated robot sensor data for the virtual surgical robot and simulated patient sensor data based on an actual state of the virtual surgical robot and the patient specific virtual anatomical model fed by the surgical simulator; and
   a machine learning unit configured to perform a machine learning process to create control data by the machine learning process, the machine learning unit reading the sensor simulator, the virtual surgical robot and the virtual surgical field and feeding the virtual surgical robot, and
   wherein the processing unit is configured to:
   generate the control data in a learning mode by simulating a surgical treatment, and
   provide the control data to the control device to control the surgical robot autonomously in the practice mode to perform the real surgical treatment on the patient.

2. The robotic surgical system according to claim 1, further comprising:
   at least one patient sensor configured to provide the patient sensor data depending on the conditions of the patient.

3. The robotic surgical system according to claim 1, wherein the at least one robot sensor is configured to provide the patient sensor data depending on the conditions of the patient.

4. The robotic surgical system according to claim 1, wherein the virtual surgical field additionally comprises simulated pre-surgical data of the patient.

5. The robotic surgical system according to claim 1, wherein the virtual surgical robot is configured to simulate the movement of the moveable robot member with a mathematic model for the moveable robot member and the at least one actuator.

6. The robotic surgical system according to claim 1, wherein, to sense the conditions in the surgical field, the at least one robot sensor comprises at least one of a white light camera, an IR camera, an OCT sensor, an ultrasonic sensor a fluorescence sensor, and a depth sensor.

7. The robotic surgical system according to claim 1, wherein the moveable robot member is an endoscope or a surgical tool.

8. A method for configuring a surgical robot being autonomously controlled in a practice mode, the method comprising:
   providing the surgical robot comprising a moveable robot member, at least one actuator for moving the moveable robot member to 6D poses in a surgical field and for driving the moveable robot member to act in the surgical field, at least one robot sensor for providing robot sensor data giving the at least one actuator a feedback signal and depending on conditions in the surgical field, and a control device configured to control the at least one actuator according to control data and under feedback of the robot sensor data, and to perform a real surgical treatment on a patient in the practice mode;

providing a patient specific virtual anatomical model including a virtual surgical field;

providing a virtual surgical robot by simulating movement and driving of the moveable robot member;

providing a surgical simulator reading the patient specific virtual anatomical model and the virtual surgical robot regarding the movement and the driving of the moveable robot member;

providing a sensor simulator creating simulated robot sensor data for the virtual surgical robot and simulated patient sensor data based on an actual state of the virtual surgical robot and the patient specific virtual anatomical model fed by the surgical simulator;

reading signals from the sensor simulator, the virtual surgical robot and the virtual surgical field and feeding signals to the virtual surgical robot in a machine learning process;

creating the control data by the machine learning process; and providing the control data to the surgical robot to control the surgical robot autonomously in the practice mode to perform the real surgical treatment on the patient.

9. The method according to claim 8, further comprising: providing at least one patient sensor outputting the patient sensor data depending on the conditions of a patient.

10. The method according to claim 8, wherein the at least one robot sensor is configured to output the patient sensor data depending on the conditions of a patient.

11. The method according to claim 8, wherein the virtual surgical field further comprises simulated pre-surgical data of a patient.

12. The method according to claim 8, wherein the providing the virtual surgical robot includes simulating the movement of the moveable robot member with a mathematic model for the moveable robot member and the at least one actuator.

13. The method according to claim 8, wherein, for sensing the conditions in the surgical field, the providing the at least one robot sensor includes providing at least one of a white light camera, an IR camera, an OCT sensor, an ultrasonic sensor, a fluorescence sensor, and a depth sensor.

14. The method according to claim 8, further comprising: providing the moveable robot member as an endoscope or a surgical tool.

\* \* \* \* \*